(12) United States Patent
Andersen et al.

(10) Patent No.: US 9,017,720 B2
(45) Date of Patent: Apr. 28, 2015

(54) POLYSACCHARIDE CAPSULES AND METHOD OF PREPARATION

(75) Inventors: Peder Oscar Andersen, Oslo (NO); Olav Gåseröd, Steinberg (NO); Christian Klein Larsen, Leirsund (NO)

(73) Assignee: FMC Bioploymer AS, Sandvika (NO)

( * ) Notice: Subject to any disclaimer, the term of this patent is extended or adjusted under 35 U.S.C. 154(b) by 932 days.

(21) Appl. No.: 13/089,972

(22) Filed: Apr. 19, 2011

(65) Prior Publication Data

US 2011/0195101 A1     Aug. 11, 2011

Related U.S. Application Data

(62) Division of application No. 10/509,980, filed as application No. PCT/NO03/00109 on Apr. 4, 2003, now Pat. No. 7,972,620.

(30) Foreign Application Priority Data

Apr. 4, 2002   (NO) .................................. 20021592

(51) Int. Cl.
    *A61K 9/48*     (2006.01)
(52) U.S. Cl.
    CPC ............. *A61K 9/4883* (2013.01); *A61K 9/4816* (2013.01)
(58) Field of Classification Search
    CPC ...... A61K 9/48; A61K 9/4833; A61K 9/4891
    USPC .......................................... 424/455, 452, 461
    See application file for complete search history.

(56) References Cited

U.S. PATENT DOCUMENTS

| | | |
|---|---|---|
| 2,036,934 A | 4/1936 | Green |
| 2,128,551 A | 8/1938 | Legloahec |
| 2,379,817 A | 7/1945 | Mabbs |
| 2,624,069 A | 1/1953 | Fischer, Jr. |
| 3,376,199 A | 4/1968 | Coles |
| 3,498,839 A | 3/1970 | Mehta |
| 3,577,515 A | 5/1971 | Vandegaer |
| 3,682,654 A | 8/1972 | Johnson |
| 3,959,464 A | 5/1976 | De Savigny |
| 4,140,516 A | 2/1979 | Scher |
| 4,309,213 A | 1/1982 | Graber et al. |
| 4,324,683 A | 4/1982 | Lim et al. |
| 4,422,985 A | 12/1983 | Morishita et al. |
| 4,426,337 A | 1/1984 | Suzuki et al. |
| 4,481,157 A | 11/1984 | Morishita et al. |
| 4,507,327 A | 3/1985 | Ueda |
| 4,690,816 A | 9/1987 | Hata et al. |
| 4,695,466 A | 9/1987 | Morishita et al. |
| 4,702,921 A | 10/1987 | Ueda |
| 5,015,448 A | 5/1991 | Vorlop et al. |
| 5,330,835 A | 7/1994 | Kikuchi et al. |
| 5,362,564 A | 11/1994 | Suzuki et al. |
| 5,385,737 A | 1/1995 | Shigeno et al. |
| 5,418,154 A | 5/1995 | Aebischer et al. |
| 5,472,648 A | 12/1995 | Alisch et al. |
| 5,478,570 A | 12/1995 | Sunohara et al. |
| 5,629,187 A | 5/1997 | Ors et al. |
| 5,756,123 A | 5/1998 | Yamamoto et al. |
| 5,882,680 A | 3/1999 | Suzuki et al. |

(Continued)

FOREIGN PATENT DOCUMENTS

| | | |
|---|---|---|
| DE | 3913772 | 10/1990 |
| DE | 19922537 A1 | 11/2000 |

(Continued)

OTHER PUBLICATIONS

International Search Report for PCT/NO03/00109.
International Preliminary Examination Report for PCT/NO03/00109.
English language Abstract for JP-9025228.
English language Abstract for JP-61044810.
Olav Gaserod et al.; "Microcapsules of alginate-chitosan—1A quantitative study of the interaction between alginate and chitosan"; Biomaterial; vol. 19; pp. 1815-1825; 1998.

(Continued)

*Primary Examiner* — Gollamudi Kishore
(74) *Attorney, Agent, or Firm* — FMC Corporation

(57) ABSTRACT

The present invention is directed to seamless capsules and methods for making seamless capsules having a high oil content as described herein. More specifically, the present invention is directed to seamless capsules, and methods for making seamless capsules, made from a process involving the steps of: (a) preparing an emulsion comprising oil, water, an emulsifier, and at least one of a water-soluble monovalent metal salt, polyvalent metal salt, and an acid, wherein said oil is present in an amount of at least 50% by weight of said emulsion; with the proviso that said emulsion does not contain marmelo mucilage; and (b) adding portions of said emulsion to an aqueous gelling bath comprised of at least one ionic polysaccharide thereby encapsulating said portions of said emulsion in a polysaccharide gel membrane, and optionally (c) drying the resulting capsules by removing water.

Improved methods are described for preparing seamless capsules comprising oil and water emulsions containing high concentrations of oil, where the emulsions are suitable for encapsulation into capsules of a polysaccharide gel. Of particular interest are emulsions of oil and water, where the oil is present in an amount of at least 50% by weight of the emulsion and the capsule is, for example, an alginate gel. Oils that are a pharmaceutical active agent, a nutritional supplement or a food; or oils that act as a carrier therefore, are also of particular interest. According to a preferred embodiment of the present invention the emulsion may contain further solid or liquid or gaseous components and be mixed to a dispersion before the encapsulation. The capsules of the invention are suitable for a variety of applications, e.g., pharmaceutical, nutraceutical, veterinary, agricultural, cosmetic, or food applications.

45 Claims, No Drawings

(56) References Cited

U.S. PATENT DOCUMENTS

| | | | |
|---|---|---|---|
| 5,942,266 | A | 8/1999 | Okamura et al. |
| 5,976,604 | A | 11/1999 | Kunieda et al. |
| 6,106,815 | A | 8/2000 | Kang et al. |
| 6,165,615 | A | 12/2000 | Itakura et al. |
| 6,214,376 | B1 | 4/2001 | Gennadios |
| 6,251,661 | B1 | 6/2001 | Urabe et al. |
| 6,325,859 | B1 | 12/2001 | De Roos et al. |
| 6,458,818 | B1 | 10/2002 | Lipari et al. |
| 6,982,095 | B2 | 1/2006 | Asada et al. |
| 7,585,538 | B2 | 9/2009 | Mangos et al. |
| 2003/0082272 | A1 | 5/2003 | Bouwmeesters et al. |
| 2003/0219514 | A1 | 11/2003 | Jones et al. |
| 2004/0022845 | A1 | 2/2004 | Zhang |
| 2005/0095337 | A1 | 5/2005 | Kelly et al. |
| 2006/0096252 | A1 | 5/2006 | Nakamura et al. |
| 2007/0259097 | A1 | 11/2007 | Andersen et al. |

FOREIGN PATENT DOCUMENTS

| | | |
|---|---|---|
| EP | 0212875 | 4/1987 |
| EP | 0 480 729 | 4/1992 |
| EP | 0173915 B1 | 8/1992 |
| EP | 0 513 603 | 11/1992 |
| EP | 0 655 241 | 5/1995 |
| EP | 1020177 A1 | 7/2000 |
| EP | 1025842 A1 | 8/2000 |
| EP | 1 072 259 | 1/2001 |
| EP | 1690518 | 8/2006 |
| FR | 2521428 A1 | 8/1983 |
| GB | 1163023 A | 9/1969 |
| GB | 2192171 A | 1/1988 |
| HU | 53800 | 12/1990 |
| JP | 48-16183 B | 5/1973 |
| JP | 55-7241 A | 1/1980 |
| JP | 58-88027 | 5/1983 |
| JP | 58-172313 A | 10/1983 |
| JP | 59-88420 A | 5/1984 |
| JP | 61010508 | 1/1986 |
| JP | 59166916 | 3/1986 |
| JP | 61044810 | 3/1986 |
| JP | 62282772 | 5/1989 |
| JP | 01082853 | 2/1990 |
| JP | 63-265514 | 4/1990 |
| JP | 02078799 | 12/1991 |
| JP | 03280846 | 12/1991 |
| JP | 04046099 | 7/1992 |
| JP | 7196478 | 8/1995 |
| JP | 2519485 | 7/1996 |
| JP | 9025228 | 1/1997 |
| JP | 2589556 | 3/1997 |
| JP | 07297573 | 4/1997 |
| JP | 09-327501 | 12/1997 |
| JP | 09-327501 A | 12/1997 |
| JP | 2000-325431 | 11/2000 |
| LV | 11585 | 2/1997 |
| WO | WO 89/01034 | 2/1989 |
| WO | WO-99/02252 | 1/1999 |
| WO | WO-99/18938 | 4/1999 |
| WO | WO-03030874 A1 | 4/2003 |
| WO | WO-2004060356 A1 | 7/2004 |

OTHER PUBLICATIONS

Olav Gaserod et al.; "Microcapsules of alginate-chitosan. II. A study of capsule stability and permeability"; Biomaterials; vol. 20; pp. 773-783; 1999.

"Liquid Core Hydrocolloid-Oil Capsules Produced in a Single Step", Nussinovitch, et al., Food Hydrocolloids, 1997, 11, 209, pp. 325 to 331.

P. Spiekermann, et al., (1987), "Animal Cells Encapsulated within Ca-Alginate Hollow-Spheres", Proc. 4$^{th}$ European Congress on Biotechnology; vol. 3, pp. 590-593; Elsevier Science Publishers B.V., Amsterdam, Printed in the Netherlands.

Research Article "A Novel, Self Correcting Membrane Coating Technique", Hitesh R. Bhagat, Pharmaceutical Research, vol. 8, No. 5, 1991, pp. 576-583.

"Cell Immobilization within Coated Alginate Beads or Hollow Fibers Formed by Ionotropic Gelation", Vorlop, et al., 1987, Enzyme Engineering, 8, pp. 339-342.

Patel, et al. (2000) "A Novel Encapsulation Technique for the Production of Artificial Seeds", Plant Cell Reports, 19, 868-874.

POLYSACCHARIDE CAPSULES AND METHOD OF PREPARATION

The present invention pertains to oil-containing seamless capsules having a polysaccharide gel membrane on the outer surface thereof, and methods for preparation of such capsules. The inventive capsules are suitable for pharmaceutical, nutraceutical, veterinary, food, agricultural and specialty applications such as paintballs.

BACKGROUND OF THE INVENTION

It is well known that gelatin has been used, inter alia, in a wide range of food products, such as gelatin containing courses, compressed meats, pastries, and the like. It is also well known that gelatin has been used to deliver pharmaceuticals in capsule form for more than one hundred years. It has many useful physical and chemical properties, which support this broad range of utility.

The primary sources of gelatin are from bovine animals and pigs. The source of gelatin can be a problem for potential areas of use or for particular consumers. Large groups of people around the world cannot ingest any products derived from these animals, because of religious beliefs or because of dietary requirements and preferences. Additionally, as there has recently been at least one alleged instance of cross-species contamination from cattle to humans (at least one alleged instance with bovine spongiform encephalopathy, BSE, or "Mad Cow Disease" in the United Kingdom), the use of uncontrolled by-products from animals has lost some level of commercial acceptance. It has become apparent that replacement compositions for gelatin, which are not derived from animals, are desirable.

For example, U.S. Pat. No. 5,942,266 ('266 patent) sets forth one method for capsule formation using alginates which comprises contacting liquid drops of a composition of an aqueous solution of a water-soluble macromolecular substance (such as guar gum) at least a portion of which is marmelo mucilage, an oleaginous substance (such as animal or vegetable oil), a water-soluble polyvalent metal salt (such as calcium chloride), with an aqueous solution of a water-soluble salt of an alginic acid, thereby forming a water-insoluble film of alginic acid salt on the outer surface of the liquid drop. As reported in the '266 patent, the amount of oleaginous substance that is encapsulated can be in the range of 10% to 95% by weight of the liquid drop. In order to encapsulate such a relatively large amount of oleaginous substance (preferably 30-85% by weight of the liquid drop), the composition of the liquid drop in the '266 patent is very complex; requiring the presence of exacting amounts of macromolecular substance, oleaginous material, polyvalent metal and other salts; and the essential requirement of marmelo mucilage. The oil-entrapment with the use of marmelo mucilage led to formulations where separation began after only 30 minutes, confer column 6, lines 27-30.

JP patent application no. 59166916 describes enteric soft capsules obtained by dual nozzles techniques. These techniques are limited to the provision of spherical capsules. Another frequent problem with capsules prepared by these techniques is capsules with walls of uneven thickness, due to density differences of the different phases during preparation.

JP 6055060 and JP 6079165 concern seamless coating film capsules containing surfactant and detergent preparation obtained by the use of multiple nozzles technique.

Thus, it can be seen that an improved, simpler method is needed for preparing stable robust seamless capsules comprising relatively large amounts of active materials.

Other references such as U.S. Pat. No. 4,702,921 disclose the preparation of capsules containing alginate gel membranes, but appear to use an amount of water that makes the capsules difficult to dry.

The present inventors have overcome the problems associated with the prior art wherein the capsules contain too much water.

It has now been found in accordance with the present invention that emulsions comprised of relatively large amounts of an active material, such as an oil, or added other component, can be prepared that offer an alternative to complex combinations of active material, water, and a plurality of other components. Accordingly, the objects of the present invention include: 1) a method of preparing seamless capsules of high stability, using water emulsions containing relatively large amounts of oils, 2) a simple method of preparing seamless capsules of high stability that encapsulate the aforementioned water emulsions of oils with other solid, or liquid or gaseous components added, in a polysaccharide gel membrane, and 3) optionally, a method of drying and coating the polysaccharide capsules of emulsion for a subsequent use. Furthermore the shape of the capsules of the present invention can be determined prior to the preparation, and the capsules of spherical, oval, oblong or cylindrical shape prepared according to the methods of the present invention have an uniform wall thickness. The capsules of the present invention have an excellent integrity and storage stability over a prolonged period of time.

SUMMARY OF THE INVENTION

Specifically, this invention is directed to a method for preparing seamless capsules having a polysaccharide gel membrane on the outer surface comprising the steps of (a) preparing an emulsion of oil, water, an emulsifier, and at least one of a water-soluble monovalent metal salt, polyvalent metal salt, and an acid, wherein the oil is present in an amount of at least 50% by weight of the emulsion; with the proviso that the emulsion does not contain marmelo mucilage, and (b) adding portions of the emulsion to an aqueous gelling bath comprised of at least one ionic polysaccharide, thereby encapsulating the portions of emulsion in a polysaccharide gel membrane, and optionally (c) drying the resulting capsules by removing water.

The present invention is also directed to seamless capsules obtained by this method.

In a preferred embodiment of the invention, the method of preparing seamless capsules further comprises the step of adding a further solid, or liquid or gaseous component prior to step b) to at least one of said oil, water, emulsifier and at least one of water-soluble monovalent metal salt, polyvalent metal salt, and acid prior to or after formation of the emulsion and mixing to a dispersion.

The present invention also comprises seamless capsules thereby obtained. The capsules of the invention can be made in a variety of shapes.

DETAILED DESCRIPTION OF THE INVENTION

Surprisingly, it has now been found that relatively simple water emulsions containing relatively large amounts of oils can be encapsulated in polysaccharide gel capsules. A method of preparing the seamless capsules having a polysaccharide gel membrane on the outer surface comprises the steps of: (a) preparing an emulsion comprising oil, water, an emulsifier, and at least one of a water-soluble monovalent metal salt, polyvalent metal salt, and an acid, wherein the oil is present in an amount of at least 50% by weight of the emulsion; with the proviso that the emulsion does not contain marmelo mucilage, and (b) adding portions of the emulsion to an aqueous gelling bath comprised of at least one ionic polysaccharide thereby encapsulating the portions of the emulsion in a polysaccharide gel membrane, and optionally (c) drying the resulting capsules.

The present invention requires the oil to be present in an amount of at least 50% by total weight of the emulsion. This means that the oil content is calculated based on the total weight of the oil, water, emulsifier and water-soluble monovalent metal salt, polyvalent metal salt and acid. The emulsion of the present invention can be used as a carrier or vehicle for a variety of ingredients as discussed below. It should however be clear that the at least 50% oil content does not take into account the amount of any other components added prior to or after formation of the emulsion.

The oil and water emulsion that can be encapsulated within the scope of the present invention is an emulsion wherein the oil is selected from any oil, or combination of oils, that find utility in an encapsulated form, for example, for use in the pharmaceutical (pharmaceutical herein includes veterinary and nutraceutical), food, nutritional, cosmetic, agricultural, and the like industries. Suitable oils include, without limitation, oils derived from animals, plants, microorganisms, or extracts thereof; oils that are chemical compounds derived by synthetic or other means, or formulations thereof; oils that are fatty acids, esters, or derivatives thereof; or oils that may be a pharmaceutically active agent, a nutritional supplement, flavor oil, or a food. Oils within the scope of the present invention also include oils that act as carriers or solvents for oil-soluble active materials such as an oil-soluble pharmaceutically active agent, a nutritional, flavor, fragrance, supplement, or a food. Other oils within the scope of the present invention are those that include naturally occurring emulsifiers. One such oil is soy oil, which contains lecithin. Lecithin is useful in food manufacturing as an emulsifier in products high in fats and oils. Preferred oils within the scope of the present invention are those that are a liquid, or that can be made into a liquid at a temperature in the range of, for example, 20° C. to 95° C.

An emulsion of oil and water is defined as a heterogeneous system, wherein the oil and water are immiscible and either 1) the water is intimately dispersed in the oil, or 2) the oil is intimately dispersed in the water, in which the dispersed material is in the form of droplets. If left alone, the dispersed droplets will coalesce to form larger and larger droplets, until all of the dispersed phase has coalesced. Emulsifying agents, or emulsifiers, are used to preserve the integrity of the dispersed droplets and prevent the separation of the two phases. To enable emulsifiers to prevent the separation of the oil phase and the water phase, the emulsifiers preferably have distinct chemical characteristics. Among the preferred characteristics of an emulsifier are that they possess 1) hydrophilic (water-soluble) and 2) lipophilic (oil-soluble) groupings in their molecular structures. The effectiveness of an emulsifier depends upon the balance of the weight-average molecular weight of the hydrophilic and lipophilic groups. The balance, i.e., the hydrophilic-lipophilic balance (hereinafter termed "HLB") has a value that can range from 1 upwards. In general, emulsifiers with lower HLB values, for example 3-9, are more suitable for preparing water-in-oil emulsions, whereas emulsifiers with higher HLB values, for example 9-18, are more suitable for preparing oil-in-water emulsions; however, there are emulsifiers that are useful for both types of emulsions.

Emulsifiers suitable in the context of the present invention are chemical compounds having both a hydrophilic group and a lipophilic group wherein the HLB value is in the range of 1 to 19. Examples of such emulsifiers having HLB values in the range of 1 to 19 include, without limitation, glycerin fatty acid esters, lactic acid esters of monoglycerides, lecithins, polyglycerol polyricinoleate, sorbitan esters of fatty acids, succinic acid esters of monoglycerides, calcium stearoyl dilactate, citric acid esters of monoglycerides, diacetyl tartaric acid esters of monoglycerides, polyoxyethylene sorbitan esters of fatty acids, sucrose esters of fatty acids, and other emulsifiers. Emulsifying agents may also include some particulate materials, such as, for example, soot (water-in-oil emulsion stabilizer) or silica powder (oil-in-water emulsion stabilizer) as generally known. Preferred emulsifiers of the present invention are selected from the group of polyoxyethylene(20) sorbitan monolaurate (Sold under the name TWEEN 20) polyglycerol polyricinoleate (Sold under the name and trademark of PGPR 90, by Danisco, Copenhagen, Denmark), calcium stearoyl-2-lactylate (Sold under the name and trademark of VERV K, by American Ingredients Company, Kansas City. MO, USA), sorbitan monooleate (Sold under the name and trademark of SPAN 80, by Aldrich Chemical, Milwaukee, Wis., USA), and mixtures thereof. More preferred emulsifiers are polyoxyethylene(20) sorbitan monolaurate, polyglycerol polyricinoleate, or mixtures thereof.

The emulsions of oil and water of the present invention contain at least one of a water-soluble monovalent metal salt, a polyvalent metal salt, or an acid. For example, polysaccharides, such as alginates gel at low pH, so acids, e.g., dissociated hydrogen ions, can be used in the present invention as gelling agents. A water-soluble monovalent metal salt, polyvalent metal salt, or acid suitable for use in the present invention includes any inorganic or organic salt or acid that is capable of disassociating into a free ionic state in water, where the ions are capable of forming a gel with an ionic polysaccharide. Suitable salts include, without limitation, the salts of sodium, potassium, calcium, strontium, barium, aluminum, magnesium, other salts, and mixtures thereof. A preferred salt is calcium chloride, in either hydrated or anhydrous form. Increasing the salt content in the oil and water emulsion, inter alia, increases the thickness of the polysaccharide gel membrane when the capsules are formed, thereby making the capsules stronger. The salt in the oil and water emulsion is present in at least a gel-forming amount sufficient to adequately form polysaccharide gel membranes surrounding portions of the oil and water emulsion. Preferably, within the scope of the present invention, the salt is present in the oil and water emulsion in an amount of up to 25% by weight of the emulsion, more preferably from 2% by weight to 15% by weight of the emulsion.

In a first embodiment of the present invention, the emulsion is an oil-in-water emulsion. The emulsion can be prepared by dissolving a monovalent or polyvalent metal salt (as discussed above), for example, calcium chloride dihydrate and at least one emulsifier (as discussed above) for example, polyoxyethylene(20) sorbitan monolaurate, in water. The resultant solution may then be homogenized during which time an oil, for example, fish oil, soy oil, oleic acid, or mineral oil, can be slowly added to form a highly viscous oil-in-water emulsion. A preferable amount of oil present in the oil-in-water emulsion is in an amount of 70% by weight to 98% by weight of the oil, water, emulsifier and water-soluble monovalent metal salt, polyvalent metal salt and acid, more preferably, in an amount of 85% by weight to 95% by weight of the oil, water, emulsifier and water-soluble monovalent metal salt, polyvalent metal salt and acid.

In a second embodiment of the present invention, the emulsion is a water-in-oil emulsion. The emulsion can be prepared by adding a water solution of a monovalent or polyvalent metal salt (as discussed above) and at least one emulsifier (as discussed above), for example, polyglycerol polyricinoleate, to an oil (as discussed above) during which time the mixture can be homogenized to provide the water-in-oil emulsion. A preferable amount of oil present in the water-in-oil emulsion is in an amount of 65% by weight to 85% by weight of the oil, water, emulsifier and water-soluble monovalent metal salt, polyvalent metal salt and acid, more preferably, in an amount of 70% by weight to 80% by weight of the oil, water, emulsifier and water-soluble monovalent metal salt, polyvalent metal salt and acid. As set forth above, soy oil contains the naturally occurring emulsifier lecithin. Water-in-oil emulsions of soy oil may be stable for a period of time long enough so that the emulsion can be encapsulated without inclusion of additional emulsifier.

In a third embodiment of the present invention, the emulsion is a water-in-oil-in-water emulsion. A water-in-oil-in-water emulsion provides a means for encapsulating not only an oil, or an oil-soluble substance, but also, a water-soluble substance, or a water-soluble active ingredient. Accordingly, an inner phase comprised of a solution of a water-soluble substance in water can be added to a middle phase comprised of an oil (as discussed above) and an emulsifier (as discussed above), for example, polyglycerol polyricinoleate, during which time the mixture can be homogenized to form a water-in-oil emulsion. The so-formed water-in-oil emulsion may then be added to an outer phase comprised of a water solution of a monovalent or polyvalent metal salt (as discussed above) and an emulsifier (as discussed above), for example, polyoxyethylene(20) sorbitan monolaurate, during which time the mixture can be homogenized to form a highly viscous water-in-oil-in-water emulsion. A preferable amount of oil present in the water-in-oil-in-water emulsion is in an amount of 60% by weight to 90% by weight of the oil, water, emulsifier and water-soluble monovalent metal salt, polyvalent metal salt and acid, more preferably, in an amount of 70% by weight to 80% by weight of the oil, water, emulsifier and water-soluble monovalent metal salt, polyvalent metal salt and acid.

A preferred emulsion in the context of the present invention is an oil-in-water emulsion as discussed above in the first embodiment. A drying process at an elevated temperature, for example, at about 60° C., to remove water from the oil-in-water emulsion prior to its encapsulation can eliminate a large portion of water from the encapsulation step, thereby providing a capsule in a relatively dry form, if a capsule in dry form is desired. The length of a separate capsule-drying step can therefore be shortened. Additionally, as an aid to shortening the length of a capsule-drying step if one is desired, some of the water in the emulsion can be replaced with a water-miscible solvent, for example an alcohol of $C_1$-$C_4$ straight or branched carbon length, for example, ethanol.

In a preferred embodiment, the invention is directed to a method of preparing seamless capsules having a polysaccharide gel membrane on the outer surface, comprising the steps of preparing an emulsion comprising oil, water, an emulsifier, and at least one of a water-soluble monovalent metal salt, polyvalent metal salt, and an acid, wherein said oil is present in an amount of at least 50% by weight of said emulsion; with the proviso that said emulsion does not contain marmelo mucilage; and further comprising the step of adding a further solid, liquid or gaseous component prior to step b) to the at least one of oil, water, emulsifier, and at least one of a water-soluble monovalent metal salt, polyvalent metal salt, and acid prior to or after formation of the said emulsion and mixing to a dispersion; and adding portions of the said dispersion to an aqueous gelling bath comprised of at least one ionic polysaccharide thereby encapsulating said portions of said dispersion in a polysaccharide gel membrane, and optionally drying the resulting capsules by removing water.

The added components can be added to at least one of oil, water, emulsifier, and at least one of a water-soluble monovalent metal salt, polyvalent metal salt, and acid of the emulsion, prior to or after emulsification. These further components may include one or more of a pharmaceutical agent, veterinary agent, a nutritional supplement, an agricultural agent, a food, a cosmetic ingredient, or excipient. Also living material such as cell lines and micro organisms; probiotics and enzymes may be included in the capsules of the invention. Suitable pharmaceutical active agents include without limitation an oil-soluble or insoluble drug, and drugs with a higher water solubility such as Paracetamol, and Verapamil HCl. Suitable nutritional supplements include herbs, roots, leafs, fruits, flowers, grasses, barks, fruit peels, and minerals or trace minerals in ionic or elemental form, such as calcium, magnesium, zinc, selenium and iron. Suitable agricultural active agents include herbicides and insecticides. Other suitable components include, without limitation, dyes; colorants and pigments such as titanium dioxide and calcium carbonate; plasticizers, such as glycerol, sorbitol, maltitol and polyethylene glycols; stabilizing polymers, such as chitosan; cellulose gums, carrageenan, alginates, propylene glycol alginate, gellan, xanthan gum, locust bean gum, guar, pectins, gum arabic, gum tragacanth, sodium-carboxymethylcellulose, alkyl cellulose ethers such as hydroxypropylmethylcellulose, hydroxypropylcellulose, hydroxyethylcellulose and methylcellulose and agar-agar; preservatives such as lower alkylparabens, benzoic acid, sodium benzoate, and benzyl alcohol; antioxidants such as ascorbic acid, ascorbyl palmitate, sulfites, L-tocopherol, butylated hydroxyanisole and propyl gallate; disintegrating compounds, and other components.

The further components can be added in liquid form, such as simethicone or vitamin E (α-tocopherol); in gaseous form such as carbon dioxide and other gases and as solids such as calcium carbonate and insoluble drugs. The solid components can be crystalline or non-crystalline and in the form of powders, fibers, particles, nanoparticles or granules.

Advantages of adding the components to the emulsion include for example the ability to add large amounts of active ingredient just prior to the gelation process and to minimize contact with elevated temperatures, water and high shear environment, as this can destroy some components by for example decomposition, oxidation and re-crystallization. As a result, the seamless capsules of the present invention can be pharmaceutical, veterinary, agricultural or nutraceutical solid dosage forms and can be used in specialty applications such as paintballs or as a cosmetic product such as bath oils, etc.

Depending on the emulsion used and the components added, the seamless capsules can be manipulated to control the release of the active ingredient as desired in its end-use, e.g. in vivo the capsules can be in a form of immediate or delayed release.

The added solid, liquid or gaseous components are mixed, prior to or after emulsification of the oil, water, an emulsifier, and at least one of a water-soluble monovalent metal salt, polyvalent metal salt, and an acid, to form a dispersions, and they will appear in amounts of up to 85% by weight of the dried capsule. Preferably, the amounts of components added to the emulsion is present in amounts from 30%-85% by weight of the dried capsule.

Capsules having a polysaccharide gel membrane on the outer surfaces are formed by adding portions of any one of the oil and water emulsions, or dispersions thereof set forth above to an aqueous gelling bath comprised of at least one ionic polysaccharide, thereby encapsulating the portions of the emulsion, or dispersion in a polysaccharide gel membrane. The polysaccharide gel membrane formed around the portions of the emulsion, or dispersion is the reaction product of ions of the water-soluble monovalent metal salt, polyvalent metal salt or acid that are in the emulsion, with an ionic polysaccharide that is in the gelling bath. A preferred concentration of ionic polysaccharide in the gelling bath is in the range of 0.1% to 10%, more preferably in the range of 0.5% to 7% by total weight of the gelling bath solution.

Suitable polysaccharides in the context of the present invention include carrageenans such as kappa, kappaII and iota carrageenans, alginates, chitosans, pectins such as low methoxy and amidated low metoxy pectins, sodium-carboxymethylcellulose, propylene glycol alginate, or mixtures thereof; however, a preferred polysaccharide is an alginate.

Alginates, derived from, inter alia, brown seaweeds (*Phaeophyceae* sp.) are linear unbranched chemical polymers containing (1-4)-linked β-D-mannuronic acid (M) and α-L-guluronic acid (G) residues. Alginates are not random copolymers, but consist of blocks of similar and alternating residues, for example, MMMM, GGGG, and GMGM, and are generally useful in the form of alginic acid or salts thereof.

A suitable alginate in the gelling bath is an alginate having a weight-average molecular weight of 20,000 Daltons to 500,000 Daltons, having a G-content of at least 30%, preferably in the range of 40% to 80%, or 50% to 90%. As used throughout, the weight-average molecular weight is calculated by first determining the intrinsic viscosity, then using the Mark-Houwink Sakurada Equation, as in Martinsen, et al; "Comparison of Different Methods for Determination of Molecular Weights and Molecular Weight Distribution of Alginates" (Carbohydr. Polym. 15: 171-193). It has been found that a mixture of both low and higher weight-average molecular weight alginates in the gelling bath impart preferable properties to the alginate gel capsule membrane surrounding the emulsion. For example, a preferred mixture of alginates is comprised of (i) an alginate having a low weight-average molecular weight of 30,000 Daltons to 40,000 Daltons, and (ii) an alginate having a higher weight-average molecular weight of 150,000 Daltons to 500,000 Daltons. Increasing the ratio of a higher weight-average molecular weight alginate provides a more elastic alginate gel capsule. Increasing the ratio of the low weight-average molecular weight alginate provides a less viscous gelling bath and a more favorable rate of capsule formation. Depending upon the characteristics desired in the alginate gel membrane to be formed around the emulsion, a suitable ratio of low weight-average molecular weight alginate (i) to higher weight-average molecular weight alginate (ii) in the gelling bath is in the range of 0.1 to 20 of (i) to 1 of (ii) (0.1-20:1), respectively. A preferred ratio of low weight-average molecular weight alginate (i) to higher weight-average molecular weight alginate (ii) is in the range of 1 to 16 of (i) to 1 of (ii) (1-16:1), respectively. The gelling bath may contain additional components to include, without limitation, dyes, colorants, secondary film formers, plasticizers; such as glycerol, sorbitol, maltitol and polyethylene glycols; emulsion destabilizers, density adjusters, preservatives, antioxidants, solids, disintegrants, antifoaming agents and other components.

The methods by which the oil and water emulsions, or dispersions are added to the gelling bath, inter alia, control the size of the capsules formed. The emulsion, or dispersion which can be in the form of a thick paste or in the form of a liquid of low viscosity, can be fragmented, or shaped in some manner into portions, either prior to, or simultaneously with, its addition to the gelling bath. Suitable methods for adding the emulsion, or dispersion to the gelling bath include, without limitation, dropping the emulsion from a pipette, or a nozzle, extruding the emulsion through a chopping mechanism, molding the emulsion in a casting mold, and other methods.

The seamless capsule of the invention can be made in a variety of shapes. The shape of the formed capsules can be determined by the method of adding the emulsion or dispersion to the gelling bath and by the specific composition of said emulsion or dispersion. When dropping a low viscosity composition from a pipette the shape of the end capsules will be spherical, whereas dropping higher viscosity compositions can yield oval like capsules. Highly viscous compositions can advantageously be molded or extruded. When using a mold the mold can be selected to give spherical, oval and oblong capsule shapes. When extruding through a nozzle and cutting with a cutting device, for example a knife, wire, water jet, laser or an iris shutter-like device, the shape of the capsules can be determined by the diameter of the hole and length of the cut emulsion fragment. If the diameter of the hole is in the range of the length of the fragment, the shape of the capsules can be spherical, and if the length of the fragment exceeds the diameter of the hole the shape of the capsules will be oval, oblong or cylindrical in shape. Due to the gelation process, the gelled membrane formed on the surface of the fragments added to the gelling bath, will undergo a certain amount of contraction, whereas sharp edges will be rounded off. The amount of contraction is influenced by the viscosity of the emulsion or the amount of component added to the emulsion vehicle.

The surface of the portions of the emulsion to be added to the gelling bath may be reduced in stickiness prior to adding such to the gelling bath. A reduction in the stickiness of the surface of the portions of the emulsion may aid in helping to (a) ensure the complete release of the portions from any device used to form, shape (for example, a mold), or transfer the portions to the gelling bath; (b) increase the ease and speed of handling the portions; and/or (c) avoid agglomeration or sticking of the individual portions of the emulsion as they are initially added to the gelling bath. The surface of the portions of the emulsion may be reduced in stickiness by any suitable method that does not interfere with the formation of the polysaccharide gel membrane surrounding the portions of emulsion once they are added to the gelling bath. Such suitable methods to reduce stickiness of the surface of portions of the emulsion include, without limitation, i) surface-drying, or ii) surface-hardening each portion of the emulsion, or by iii) applying a surface coating to at least part of each portion of the emulsion. Suitable surface coatings, such as release agents, anti-tacking agents and lubricants include, without limitation, polysaccharides, such as alginates, and other polysaccharides; $C_{10}$-$C_{15}$ alkyl lactates, such as lauryl lactate; calcium silicate, dioctyl malate, magnesium carbonate, D-mannitol, silica, hydrated silica, talc; oils and hydrated oils, such as castor oil, coconut oil, cottonseed oil, palm oil, soybean oil, jojoba oil, apricot oil, kernel oil, mineral oil, olive oil, sesame oil, walnut oil, wheat germ oil, and other oils; waxes, such as lanolin wax, and other waxes; microcrystalline cellulose; stearates, such as isocetyl stearate, isocetyl stearoyl stearate, isopropyl stearate, magnesium stearate, zinc stearate, and other stearates; glycerol derivatives, such as glycerol behenate, glycerol cocoate, glycerol dioleate, glycerol dioleate SE, glycerol distearate, glycerol distearate SE, glycerol laurate SE, glycerol oleate SE, glycerol polymethacrylate, glycerol ricinoleate SE, and other glycerol derivatives; fatty acids, such as palmitic acid, lauric acid, stearic acid, and other fatty acids; polyethyleneglycol (PEG) and derivatives, such as PEG-6, PEG-100, PEG-200, PEG-40 stearate, and other polyethyleneglycol derivatives; combinations thereof, and other surface coatings. More preferably, alginates may be used as the surface coating. In a preferred method, a portion of the emulsion, or dispersion may be shaped, for example, in a mold, wherein at least a part of the mold may be treated with a suitable surface coating, such as an alginate, prior to molding the portion of emulsion, or dispersion thereby imparting a surface coating to at least part of the portion of emulsion, or dispersion. The mold may be treated with an aliquot of the gelling bath containing an alginate into which the portions of emulsion, or dispersion are to be added, or the mold may be treated with different solutions of an alginate.

In certain capsule-forming methods, the portions of the emulsion, or dispersion may be added, or deflected in some manner, to the gelling bath at a point below its surface. Preferably, the gelling bath is stirred at a rate sufficient to prevent the capsules from sticking together as they are forming.

During the step of encapsulating the oil and water emulsion, or dispersion as set forth above, it is preferable that the gelling bath be maintained at a temperature of at least 20° C., and, more preferably in the range of 30° C. to 70° C. Advantageously, the gel membrane formed can have a higher alginate solids level when performing the encapsulating step at an elevated temperature. In addition, increasing the temperature may increase the rate of gelation and subsequently lower processing times, and also provides capsules with an improved, shiny appearance. If a secondary film former is preferred in the gelling bath as set forth above, it can be advantageous to add it to the gelling bath at the aforementioned range of elevated temperatures. Solutions of certain suitable secondary film formers, such as kappa-, kappaII and iota-carrageenans and agar-agar, form gels at ambient temperature, but are liquids at elevated temperatures. The liquid secondary film former, when fully dissolved in the gelling bath, becomes an integral part of the polysaccharide gel capsule, once the capsule forms. Upon cooling, the secondary film-former can solidify, or gel, thereby providing added strength to the capsule. Varying concentrations of secondary film-former provide varying levels of capsule strength.

Characteristics desired in the capsule can be optimized during the step of encapsulating by one skilled in the art, depending on the materials used. In general, this step can be accomplished during a period of time up to 240 minutes from the start of the addition of portions of the oil and water emulsion, or dispersion preferably during 2 minutes to 60 minutes, and more preferably, during 5 minutes to 20 minutes. Capsules prepared by the methods set forth above have a capsule diameter in the range of 1 millimeter to 40 millimeters, although the diameter of the capsule prepared is not restricted by the method of preparation. Gel membrane thickness of capsules prepared by the methods set forth above generally is in the range of 0.3 millimeter to 4 millimeters.

Depending upon the intended end-use of the capsules of the present invention, it may be preferable that the capsules be dry. In a drying step, the water that is contained in the now-encapsulated oil and water emulsion and water within the gel membrane itself is removed. Once "dried", the capsules are considered to be in a "dry form", although one skilled in the art will understand that a capsule in dry form can include some water, for example, up to about 20%. Preferably the water content of the capsules is less than 10% by the total weight of the dried capsules. Once dried, the polysaccharide gel membrane of the capsule becomes firmer, as it shrinks to form a thinner dry polysaccharide gel film on the outer surface of the capsule. Preferably the contents within the capsule, after drying is present in the amount of at least 70% by weight of the capsule, more preferably at least 90% by weight. Capsules prepared by the methods of the present invention, comprised of the quantities of contents set forth above advantageously do not lose their shape upon drying and therefore appear smooth, and seamless. Also in capsules containing the emulsion, possibly added a further liquid component, the core changes from non-transparent to transparent as the water in the emulsion, or dispersion is removed during the drying step. The emulsion can during the drying step completely separate into a clear oily phase, due to destabilization of the emulsion, or it can dry by dehydrating and thereby keeping the structure of the encapsulated emulsion. A smooth and seamless appearance is preferable when the capsules are to be used, inter alia, as a dosage of a pharmaceutical, a nutritional supplement, a foodstuff, an agricultural product, a fertilizer, or the like. The drying step can be accomplished by any method which provides capsules in a dry form, such as, without limitation, drying of capsules exposed to the atmosphere, drying of capsules in a fluidized bed apparatus, drying of capsules in a perforated coating pan, and other methods of drying known in the art.

Additionally, again depending upon the intended end-use of the capsules of the present invention, it may be advantageous that the capsules be coated with, for example, a secondary film-former, or a sequestrant, or a secondary film-former and a sequestrant. Coating of capsules of the present invention is preferred, for example, when dissolution properties of the so-formed capsules need to be altered, when water and mammalian body solubility need to be altered, to increase capsule strength, to change the color of the capsules, to alter the gas permeability of the capsules, and for other purposes known by one skilled in the art. Secondary film-formers include, without limitation, gelling or non-gelling polymers, and enteric polymers for example, alginates, propylene glycol alginate, carrageenans, pectins such as high methoxy (HM), low methoxy (LM), and amidated low methoxy pectins, chitosans, sodium carboxymethylcellulose, carboxymethylcellulose, cellulose acetate phthalate, cellulose acetate succinate, methyl cellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer and other enteric polymers, cetyl hydroxyethyl cellulose, hydroxypropylmethylcellulose, hydroxypropylcellulose, hydroxyethylcellulose, methylcellulose and other cellulose derivatives, lanolin wax, polyvinyl acetate, polyvinyl pyrrolidone, polyvinyl alcohol, guar gum, acacia gum, gellan gum, locust bean gum, xanthan gum, gum tragacanth, starches, maltodextrins, and other secondary film-formers.

The capsule dissolution profiles can be modified to be immediate release or enteric or delayed release, dependent on the type of polysaccharide and other materials such as secondary film formers that are used, as well as the amounts of such. The definitions of "enteric", "immediate release" and "delayed release", are those established by the US Pharmacopoeia, and such definitions are hereby incorporated by reference. The polysaccharides, secondary film formers and other materials that can be used to modify such properties are also disclosed in the US Pharmacopeia and examples of such are incorporated herein by reference. Examples of secondary film formers of enteric type include cellulose acetate phthalate, cellulose acetate succinate, methyl cellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, or mixtures thereof. Secondary film formers of immediate release include compounds such as propylene glycol alginate, polyvinyl alcohol, carrageenans, pectins, chitosans, guar gum, gum acacia, sodium carboxymethylcellulose, hydroxypropylmethyl cellulose, hydroxypropylcellulose, methylcellulose, starches, maltodextrins or mixtures thereof. The secondary film formers can be added to the gelling bath in an amount of up to 40% by weight of the said gelling bath.

Sequestrants include, without limitation, sodium citrate, phosphate salts, ethylenediaminetetraacetic acid and salts (EDTA), ethylene glycol-bis(β-aminoethyl ester)-N,N,N',N'-tetraacetic acid (EGTA), and other sequestrants. Washing the capsules with an aqueous solution of alcohol and sequestrants can also be used to increase the water solubility of the capsules.

The capsules of the invention might be washed or rinsed with an aqueous solution such as water, or an aqueous alcohol solution after the encapsulation step, and prior to the optional drying and coating step. The washed or rinsed capsules of the invention might also possibly be transferred to a hardening bath, before they are dried and coated.

Although the drying and coating of the capsules can be done separately and in no special order, a preferred method in the context of the present invention is to conduct the drying step and coating step simultaneously. The simultaneous drying and coating of the capsules can be accomplished, for example, by 1) subjecting the wet capsules to pre-drying for a short period of time (about 10 minutes) in a fluidized bed apparatus, 2) adding a solution of a coating, then 3) subjecting the coated capsules to another, usually longer drying period, affording the capsules in dry form. A "fluidized bed apparatus" is a device that can be used for drying and/or coating capsules, in which the capsules are placed in a stream of air (the fluid) at a velocity to cause the capsules to float in the stream of air, thereby causing them to dry. One such device is sold under the name and trademark of STREA-1, manufactured by Niro-Aeromatic Ltd, Hauptstrasse 145, CH-4416 Bubendorf, Switzerland.

The capsules of the present invention in dry form may have varying capsule diameters depending on the intended use; e.g., the capsule diameter can be relatively small or somewhat larger, and be in the range of 0.5 millimeter to 35 millimeters, where the dry polysaccharide gel film generally has a thickness in the range of 40 μm to 500 μm.

It is expected that polysaccharide capsules within the scope of the present invention, prepared by methods set forth herein, could be prepared either in a continuous process, or a batchwise process, whichever method is preferable for the production of suitable capsules.

The term "plasticizer" means any compound or material which, when added to the emulsion or gelling bath, aids in binding water to the polysaccharide capsule membrane once it is formed, thereby promoting softening of the capsule membrane. Plasticizers may also be added to the emulsion in order to softening the contents of the capsules. The term "secondary film formers" means any compound or material which, when added to the gelling bath, or coated onto the capsule in a separate step, aids in altering capsule properties, for example, strength, elasticity, gas permeability, solubility, and appearance. The term "stabilizing polymers" means any compound or material which, when added to the emulsion, aids in stabilizing the oil and water emulsion by increasing the viscosity of the water-phase. The term "emulsion destabilizers" means any compound or material which, when added to the gelling bath, promotes destabilization of the emulsion in the gelling bath. The term "density adjuster" means any compound or material which, when added to the gelling bath, promotes submergence of the emulsion in the gelling bath. The term "sequestrant" means any compound or material which, when used as a capsule treatment, binds or complexes the calcium, or other gelling ions, in the polysaccharide capsule membrane or film, thereby changing the physical characteristics of the capsule, for example, making the capsules more water-soluble. The term "antioxidant" means any compound or material which, when added to the emulsion or gelling bath, aids in preventing oxidation of active ingredient, for example, an oil. The term "preservative" means any compound or material which, when added to the emulsion or gelling bath, aids in preventing bacterial growth within the capsule. The term "ambient temperature" means a temperature in the range of 20° C. to 30° C.

The term "antifoaming agent" means a compound, which prevents foaming when added to the gelling bath.

The term "dispersion" means a system in which particles of any nature, e.g. solid, liquid or gas, are dispersed in a continuous phase of a different composition or state.

The present invention is now described in more detail by reference to the following examples, but it should be understood that the invention is not construed as being limited thereto. Unless otherwise indicated herein, all parts, percents, ratios, and the like are by weight.

EXAMPLE 1

Preparation and Alginate Encapsulation of a Water-in-Oil Emulsion—Soy Oil

A solution of 15.0 grams of calcium chloride dehydrate (Merck, Germany) in 10.0 grams of water was added to a mixture of 0.0001 gram of polyglycerol polyricinoleate (Emulsifier-PGPR 90) and 75.0 grams of soy oil (Mills, Norway). The mixture was vigorously stirred for about 30 seconds using a homogenizer, affording a water-in-oil emulsion. The emulsion was then dropped portion-wise into a gelling bath comprised of 2.0 grams of higher weight-average molecular weight alginate (PROTANAL SF 200, MW=387, 000 Daltons; FMC Corporation, Philadelphia, Pa.), 16.0 grams of low weight-average molecular weight alginate (PROTANAL LFR 5/60, MW=35,000 Daltons; FMC Corporation), 20.0 grams of glycerol (plasticizer), 2.0 grams of polyoxyethylene(20) sorbitan monolaurate (emulsion destabilizer, Tween 20, Fluka), 500 grams of ethanol (96% Arcus, Norway) (emulsion destabilizer—density adjuster), and 1460 grams of water. The gelling bath was stirred at a moderate rate, while being maintained at a temperature of 22° C. The addition of emulsion was complete in about 9 minutes, after which time the so-formed capsules remained in the gelling bath during a period of about one hour. After this time, the capsules were strained from the gelling bath, and rinsed with water, providing alginate capsules having a diameter of about 4 mm. The capsules were then dried during about 18 hours on a laboratory bench with air circulating over them from a fan. Upon completion of drying, a portion of the capsules were placed in a sequestrant bath of 100 grams of a solution aqueous of 0.1 Molar trisodium citrate dihydrate(Merck), 2% glycerol, and 20% ethanol for about 90 minutes. After this time the capsules were removed from the sequestrant bath, rinsed with water, and dried as set forth above. A sample of the capsules was placed in water, where the capsules dissolved in about 15 minutes. Capsules not treated with the sequestrant did not dissolve in water.

EXAMPLE 2

Preparation and Carrageenan Encapsulation of a Water-in-Oil Emulsion—Soy Oil

An water-in-oil emulsion was prepared in a manner analogous to that of Example 1, wherein the water-in-oil emulsion was comprised of 65.0 grams of soy oil, 1.0 gram of calcium chloride dihydrate, 6.5 grams of potassium chloride (Merck), and 10.0 grams of deionized water, affording the water-in-oil emulsion. The water-in-oil emulsion was added to a gelling bath, also prepared in a manner analogous to that of Example 1, wherein the gelling bath is comprised of 4.5 grams of kappa carrageenan (FMC Corp.), 75.0 grams of ethanol (emulsion destabilizer—density adjuster), 0.3 gram of polyoxyethylene (20) sorbitan monolaurate (Emulsifier-Tween 20), and 220.2 grams of deionized water. Upon completion of addition, the so-formed carrageenan capsules were kept in the gelling bath during about a one-hour period before recovering and drying in a manner analogous to that of Example 1 affording round capsules of about 4 mm in diameter.

EXAMPLE 3

Preparation and Carrageenan-Alginate Encapsulation of a Water-in-Oil Emulsion—Soy Oil A water-in-oil emulsion was prepared in a manner analogous to that of Example 1, wherein the water-in-oil emulsion was comprised of 65.0 grams of soy oil, 16.1 grams of calcium chloride dihydrate, and 6.4 grams of deionized water, affording the water-in-oil emulsion. The water-in-oil emulsion was added to a gelling bath, also prepared in a manner analogous to that of Example 1, wherein the gelling bath was comprised of 0.75 gram of carrageenan, 0.75 gram of higher weight-average molecular weight alginate (PROTANAL SF 200), 0.30 gram of polyoxyethylene(20) sorbitan monolaurate (Emulsifier-Tween 20), 3.0 grams of glycerol, and 295.2 grams of deionized water. Upon completion of addition, the so-formed carrageenan-alginate capsules were kept in the gelling bath during about a one-hour period before recovering and drying in a manner analogous to that of Example 1, affording round capsules of about 8-9 mm in diameter.

EXAMPLE 4

Preparation and Alginate Encapsulation of an Oil-in-Water Emulsion—Soy Oil

With moderate-speed stirring using a homogenizer, 130.0 grams of soy oil was slowly added to a solution of 7.0 grams of calcium chloride dihydrate, 0.8 gram of polyoxyethylene (20) sorbitan monolaurate (Emulsifier-Tween 20) and 10.0 grams of deionized water. Upon completion of addition, the mixture was vigorously stirred for about 2 minutes using a homogenizer, affording an oil-in-water emulsion. The emulsion was then added by dropping portions of the emulsion through a nozzle (7 mm in diameter) into a gelling bath comprised of 12.0 grams of higher weight-average molecular weight alginate (PROTANAL LF 10/60; MW=180,000 Daltons; FMC Corporation), 48.0 grams of low weight-average molecular weight alginate (PROTANAL LFR 5/60), 240.0 grams of glycerol (plasticizer) and 2100 grams of deionized water. The gelling bath was stirred at a moderate rate, while being maintained at a temperature of about 60° C. The addition of the emulsion was complete in about 2 minutes. Upon completion of addition, the so-formed alginate capsules were kept in the gelling bath during about a 30-minute period. During the 30-minute period, aliquots of the capsules were removed at 5, 10, 15, and 30 minutes of time in the gelling bath. A portion of each aliquot of capsules was dried in a manner analogous to that of Example 1. The dried capsules were then analyzed for elasticity and breaking strength by subjecting samples of the capsules to compression tests using a texture analyzer (TA-XT2, manufactured by Stable Micro Systems, Vienna Court, Lammas Road, Godalming, Surrey GU7 1Y1, England). Dried and wet capsules were also analyzed for film thickness and gel thickness, respectively, by splitting samples of capsules and viewing the cross section under a light microscope (OPTIHOT, manufactured by Nikon Corporation, Fuji Building 2-3, Marunouchi 3-chrome, Chioda-ku, Tokyo, Japan). As set forth in table 1 below, the results of these tests indicate that as time in the gelling bath lengthens, elasticity of the capsules decrease; and strength to break, gel thickness before drying, and dry film thickness of the capsules increase.

TABLE 1

| Capsule | Time in Gelling Bath (Minutes) | | | |
|---|---|---|---|---|
| | 5 | 10 | 20 | 30 |
| Elasticity (Force (Kg) to Compress 0.5 mm) | 0.16 | 0.29 | 0.39 | 0.44 |
| Stength (Force (Kg) to Break) | 11.7 | 14.8 | 18.5 | 18.9 |
| Gel membrane Thickness (Before drying) (in mm) | 0.88 | 0.98 | 1.05 | 1.10 |
| Dry gel Film Thickness (in μm) | 100 | 130 | 140 | 150 |

Capsules left in the gelling bath for the entire 30-minute period were oval in shape, and were about 7 mm in diameter and 11 mm in length. The elevated processing temperature resulted in faster gelling speed, higher solids content in the gel membrane before drying, and more shiny appearing capsules after drying.

EXAMPLE 5

Preparation and Alginate Encapsulation of an Oil-in-Water Emulsion—Fish Oil

An oil-in-water emulsion was prepared in a manner analogous to that of Example 4, wherein the oil-in-water emulsion was comprised of 110.9 grams of fish oil (Møller's Cod Liver Oil, Peter Møller), 4.0 grams of calcium chloride dihydrate, 1.0 gram of polyoxyethylene(20) sorbitan monolaurate (Emulsifier-Tween 20) and 10.0 grams of deionized water, affording the oil-in-water emulsion. The oil-in-water emulsion was added to a gelling bath, also prepared in a manner analogous to that of Example 4, wherein the gelling bath was comprised of 0.6 gram of higher weight-average molecular weight alginate (PROTANAL SF 200), 4.8 grams of low weight-average molecular weight alginate (PROTANAL LFR 5/60), 15.0 grams of glycerol (plasticizer), 60.0 grams of ethanol (emulsion destabilizer) and 519.6 grams of deionized water. The gelling bath was maintained at ambient temperature during the addition of the oil-in-water emulsion. The so-formed alginate capsules were oval in shape, measuring about 8 mm in diameter by about 11 mm in length. Capsules were dried in a manner analogous to that of Example 1.

EXAMPLE 6

Preparation and Alginate Encapsulation of an Oil-in-Water Emulsion—Mineral Oil

An oil-in-water emulsion was prepared in a manner analogous to that of Example 4, wherein the oil-in-water emulsion was comprised of 111.9 grams of mineral oil (White light, Aldrich), 4.0 grams of calcium chloride dihydrate, 1.0 gram of polyoxyethylene(20) sorbitan monolaurate (Emulsifier-Tween 20) and 10.0 grams of deionized water, affording the oil-in-water emulsion. The oil-in-water emulsion was added to a gelling bath, also prepared in a manner analogous to that of Example 4, wherein the gelling bath was comprised of 0.6 gram of higher weight-average molecular weight alginate (PROTANAL SF 200), 4.8 grams of low weight-average molecular weight alginate (PROTANAL LFR 5/60), 15.0 grams of glycerol (plasticizer), 60.0 grams of ethanol (emulsion destabilizer) and 519.6 grams of deionized water. The gelling bath was maintained at ambient temperature during the addition of the oil-in-water emulsion. The so-formed alginate capsules were oval in shape, measuring about 8 mm in diameter by about 11 mm in length. Capsules were dried in a manner analogous to that of Example 1.

EXAMPLE 7

Preparation and Chitosan Encapsulation of an Oil-in-Water Emulsion—Soy Oil

An oil-in-water emulsion was prepared in a manner analogous to that of Example 4, wherein the oil-in-water emulsion was comprised of 70.0 grams of soy oil, 2.2 grams of sodium polyphosphate (Calgon) (polyvalent metal salt), 0.8 gram of polyoxyethylene(20) sorbitan monolaurate (Emulsifier-Tween 20) and 10.0 grams of deionized water, affording the oil-in-water emulsion. The gelling bath was prepared by dissolving 15.0 grams of glycerol (plasticizer) and 6.0 grams of chitosan (C1210, Pronova Biopolymer) in 279.0 grams of deionized water. A 150.0-gram aliquot of the chitosan solution was then diluted with 150.0 grams of deionized water. The oil-in-water emulsion prepared above was added dropwise to the chitosan solution. The gelling bath was maintained at ambient temperature during the addition of the oil-in-water emulsion. Upon completion of addition, the so-formed chitosan capsules were kept in the gelling bath during a 30-minute period before recovering and drying in a manner analogous to that of Example 1, affording round capsules of about 7 mm in diameter.

EXAMPLE 8

Preparation and Alginate Encapsulation of an Oil-in-Water Emulsion—Soy Oil: Coating with an Alginate Secondary Film An oil-in-water emulsion was prepared in a manner analogous to that of Example 4, wherein the oil-in-water emulsion was comprised of 115.7 grams of soy oil, 3.0 grams of calcium chloride dihydrate, 0.8 gram of polyoxyethylene(20) sorbitan monolaurate (Emulsifier-Tween 20) and 10.0 grams of deionized water, affording the oil-in-water emulsion. The oil-in-water emulsion was added to a gelling bath, also prepared in a manner analogous to that of Example 4, wherein the gelling bath was comprised of 0.6 gram of higher weight-average molecular weight alginate (PROTANAL SF 200), 4.8 grams of low weight-average molecular weight alginate (PROTANAL LFR 5/60), 15.0 grams of glycerol (plasticizer), 60.0 grams of ethanol (emulsion destabilizer) and 519.6 grams of deionized water. The gelling bath was maintained at ambient temperature during the addition of the oil-in-water emulsion. Upon completion of addition, the so-formed alginate capsules were kept in the gelling bath during a 90-minute period before recovering, affording oval capsules of about 7-8 mm in diameter and 10 mm length. The recovered capsules were then placed in a fluidized bed apparatus at ambient temperature where they were dried during about a 10-minute period. A coating solution was prepared, comprised of 7.5 grams of alginate (PROTANAL LF 10/60), 7.5 grams of glycerol (plasticizer), and 235.0 grams of water. After the 10-minute drying period, 100 grams of the coating solution was added portion-wise to the capsules, during about a 45-minute period. After a period of about 80 minutes from commencing the drying and coating procedure, the capsules were removed from the fluidized bed apparatus and placed on a laboratory bench top open to the atmosphere, where they continued to dry during about 18 hours. After this time, the capsules were analyzed for elasticity, breaking strength, and film thickness in a manner analogous to that of Example 4. An aliquot of uncoated capsules was also dried for comparison tests. As set forth in table 2 below, the results of these tests indicate that the coated capsules were about as elastic as uncoated capsules, but were about four times more resistant to breakage. The film thickness was doubled in the coated capsule.

TABLE 2

| Capsule | Uncoated | Coated |
| --- | --- | --- |
| Elasticity (Force (Kg) to Compress 0.5 mm) | 0.46 | 0.54 |
| Strength (Force (Kg) to Break) | 4.3 | 17.8 |
| Dry Gel film Thickness (in µm) | 80 | 160 |

EXAMPLE 9

Preparation and Alginate Encapsulation of an Oil-in-Water Emulsion—Soy Oil: Coating with an Alginate Secondary Film and a Sodium Citrate Sequestrant An oil-in-water emulsion was prepared in a manner analogous to that of Example 4, wherein the oil-in-water emulsion was comprised of 109.8 grams of soy oil, 3.0 grams of calcium chloride dihydrate, 0.8 gram of polyoxyethylene(20) sorbitan monolaurate (Emulsifier-Tween 20) and 10.0 grams of deionized water, affording the oil-in-water emulsion. A gelling bath was prepared, also in a manner analogous to that of Example 4, wherein the gelling bath was comprised of 1.8 grams of higher weight-average molecular weight alginate (PROTANAL SF 200), 14.4 grams of low weight-average molecular weight alginate (PROTANAL LFR 5/60), 45.0 grams of glycerol (plasticizer), and 1738.8 grams of deionized water. About 600.0 grams of the gelling bath was separated, and the oil-in-water emulsion prepared above was added to it, as set forth in Example 4.

The gelling bath was maintained at ambient temperature during the addition of the oil-in-water emulsion. Upon completion of addition, the so-formed alginate capsules were kept in the gelling bath during a 120-minute period before recovering, affording oval capsules of about 10 mm length and 7-8 mm in width. The recovered capsules were then placed in a fluidized bed apparatus at ambient temperature where they were dried during about a 13-minute period. A coating solution was prepared, comprised of 3.0 grams of alginate (PROTANAL LF 10/60), 5.2 grams of trisodium citrate dihydrate (sequestrant), and 91.8 grams of water. After the 13-minute drying period, 67 grams of the coating solution was added portion-wise to the capsules, during about a 40-minute period. After this time, the capsules were removed from the fluidized bed apparatus and placed on a laboratory bench top open to the atmosphere, where they were dried during about 18 hours. When placed in water, the capsules coated in the foregoing manner showed increased solubility after about 30 minutes. For comparison tests, an aliquot of coated and uncoated capsules were dried and analyzed in a manner analogous to that of Example 4. As set forth in table 3 below, the results of these tests indicate that the uncoated capsules were more elastic and more resistant to breakage than the coated capsules. The film thickness was more than doubled in the coated capsule.

TABLE 3

| Capsule | Uncoated | Coated |
|---|---|---|
| Elasticity (Force (Kg) to Compress 0.5 mm) | 0.43 | 0.76 |
| Strength (Force (Kg) to Break) | 9.2 | 5.6 |
| Dry Gel film Thickness (in μm) | 90 | 200 |

EXAMPLE 10

Preparation and Alginate Encapsulation of a Water-in-Oil-in-Water Emulsion—Soy Oil A water-in-oil-in-water emulsion was prepared in a two-step procedure. First a water-in-oil emulsion was prepared by adding a solution 0.6 gram of sodium bicarbonate (Prolabo) (water soluble material) in 10 grams of water to a mixture of 1.1 grams of polyglycerol polyricinoleate (Emulsifier-PGPR 90) dispersed in 90 grams of soy oil. Upon completion of addition, the mixture was vigorously stirred using a homogenizer, affording a water-in-oil emulsion. Then the water-in-oil emulsion was slowly added to a solution of 3.0 grams of calcium chloride dihydrate, 1.0 gram of polyoxyethylene(20) sorbitan monolaurate (Emulsifier-Tween 20), and 10 grams of deionized water, affording a water-in-oil-in-water emulsion. The water-in-oil-in-water emulsion was then added to a gelling bath in a manner analogous to that of Example 1, affording stable alginate gel capsules.

EXAMPLE 11

Preparation and Alginate Encapsulation of an Oil-in-Water Emulsion—Soy Oil: Shaping the Emulsion in a Mold Treated with a Surface Coating An oil-in-water emulsion was prepared in a manner analogous to that of Example 4, wherein the oil-in-water emulsion was comprised of 173.5 grams of soy oil, 4.5 grams of calcium chloride dihydrate, 1.2 grams of polyoxyethylene(20) sorbitan monolaurate (Emulsifier-Tween 20) and 15.0 grams of deionized water, affording the oil-in-water emulsion. A gelling bath was prepared, also in a manner analogous to that of Example 4, wherein the gelling bath was comprised of 0.6 gram of higher weight-average molecular weight alginate (PROTANAL SF 200), 4.8 grams of low weight-average molecular weight alginate (PROTANAL LFR 5/60), 15.0 grams of glycerol (plasticizer), and 600 grams of deionized water. A flexible, plastic mold was treated by either spraying or smearing a thin film of an aliquot of the gelling bath-alginate solution, as prepared above, into the 1 cm high by 1.5 cm wide wells of the mold. Portions of the emulsion, as prepared above, were then placed into the wells of the mold, thereby imparting a surface coating to at least part of the portions of emulsion. The portions of the emulsion were allowed to stand in the mold during a period of about 5 to 20 seconds, and then they were added to the gelling bath by inverting the mold over the gelling bath and gently squeezing the shaped portions of emulsion out of the mold. The portions of emulsion exited the mold easily, without alteration of their shape. Once in the gelling bath, alginate capsule formation proceeded in a manner analogous to that of Example 4. Capsules were removed from the gelling bath and dried, also in a manner analogous to that of Example 4. The process was repeated by spraying or smearing the mold with an aqueous 1% solution of higher weight-average molecular weight alginate (PROTANAL SF 200). The process was yet again repeated by spraying or smearing the mold with an aqueous 1% solution of low weight-average molecular weight alginate (PROTANAL LFR 5/60). In both repeat processes, the portions of emulsion exited the mold easily, without alteration of their shape.

EXAMPLE 12

Preparation and Alginate-Pectin Encapsulation of an Oil-in-Water Emulsion—Soy Oil With moderate-speed stirring using a homogenizer, 400 grams of soy oil was slowly added to a solution of 20.0 grams of calcium chloride dihydrate, 4.0 grams of polyoxyethylene (20) sorbitan monolaurate (Emulsifier-Tween 20) and 40.0 grams of deionized water. Upon completion of addition, the mixture was vigorously stirred for about 2 minutes using a homogenizer, affording an oil-in-water emulsion. The emulsion was then added as cylindrical fragments, obtained by extruding the emulsion through a hole (7 mm diameter) and manually cutting with a metal knife, into a gelling bath comprised of 12.0 grams of low weight-average molecular weight alginate (PROTANAL LFR 5/60), 18.0 grams of pectin (Grindsted AMD 780, Danisco Ingredients, USA), 60.0 grams of glycerol (AnalR, BDH, VWR International, Ltd., UK) and 510 grams of deionized water. The gelling bath was stirred at a moderate rate, while being maintained at a temperature of about 22° C. The addition of the emulsion was complete in about 2 minutes. Upon completion of addition, the so-formed alginate-pectin capsules were kept in the gelling bath for another 19 minutes. The capsules were strained from the bath and rinsed with water to remove non-reacted gelling bath. The capsules were dried in a manner analogous to Example 1, yielding oval shaped capsules with a diameter of 7 mm and a length of 14 mm. The dried capsules had a total water content of about 3.8 wt %.

EXAMPLE 13

Preparation and Alginate-Propylene Glycol Alginate (PGA) Encapsulation of an Oil-in-Water Emulsion—Soy Oil: Acid Disintegrating Capsules An oil-in-water emulsion was prepared in a manner analogous to that of Example 4, wherein the oil-in-water emulsion was comprised of 390 grams of soybean oil, 12.0 grams of calcium chloride dihydrate, 3.0 grams of polyoxyethylene (20) sorbitan monolaurate (Emulsifier-Tween 20) and 30.0 grams of deionized water, affording the oil-in-water emulsion. The oil-in-water emulsion was added to a gelling bath in a manner analogous to example 12 wherein the gelling bath was comprised of 6.0 grams of low molecular weight alginate (PROTANAL LFR 5/40 RB), 24.0 grams of low molecular weight proplylene glycol alginate (PGA) (Duckloid SLF-3, Kibun) 60.0 grams of glycerol (AnalR)(plasticizer), and 510.0 grams of deionized water. The emulsion was added to the gelling bath during 2 minutes, and kept in the bath for another 19 minutes before they were collected and rinsed briefly in water. The gelling bath was maintained at ambient temperature during the addition and encapsulation of the oil-in-water emulsion. The capsules were dried on a bench with circulated air from a fan for 48 hours, and after drying, the so-formed alginate-PGA capsules were oval in shape, measuring about 8 mm in diameter by about 13 mm in length and had a water content of 6.4%. The capsules comply with the European Pharmacopoeia disintegration test 01/2002:0016 for soft capsules using 0.1 M HCl as liquid medium.

EXAMPLE 14

Preparation and Alginate-Propylene Glycol Alginate Encapsulation of an Oil-in-Water Emulsion—Soy Oil: Acid Disintegrating Capsules An oil-in-water emulsion was prepared in a manner analogous to that of Example 4, wherein the oil-in-water emulsion was comprised of 390 grams of soybean oil, 11.0 grams of calcium chloride dihydrate, 1.5 grams of polyoxyethylene (20) sorbitan monolaurate (Emulsifier-Tween 20) and 30.0 grams of deionized water, affording the oil-in-water emulsion. The oil-in-water emulsion was added to a gelling bath in a manner analogous to example 12 wherein the gelling bath was comprised of 7.2 grams of low molecular weight alginate (PROTANAL LFR 5/40 RB), 24.0 grams of low molecular weight PGA (Duckloid SLF-3, Kibun) 60.0 grams of glycerol (AnalR)(plasticizer), 80 grams of a 75% maltitol solution (Maltisweet 3145, 75%, SPI Polyols, USA) and 428.8.0 grams of deionized water. The emulsion was added to the gelling bath during 2 minutes, and kept in the bath for another 19 minutes before they were collected and rinsed briefly in water. The gelling bath was maintained at ambient temperature during the addition and encapsulation of the oil-in-water emulsion. The capsules were dried on a bench with circulated air from a fan for 48 hours, and after drying, the so-formed alginate-PGA capsules were oval in shape, measuring about 8 mm in diameter by about 14 mm in length. The capsules comply with the European Pharmacopoeia disintegration test 01/2002:0016 for soft capsules using 0.1 M HCl as liquid medium.

EXAMPLE 15

Preparation and Alginate-Propylene Glycol Alginate Encapsulation of an Oil-in-Water Emulsion—Soy Oil: Additional Hardening in a Calcium Lactate Solution An oil-in-water emulsion was prepared in a manner analogous to that of Example 4, wherein the oil-in-water emulsion was comprised of 390 grams of soybean oil, 11.0 grams of calcium chloride dihydrate, 1.5 grams of polyoxyethylene (20) sorbitan monolaurate (Emulsifier-Tween 20) and 30.0 grams of deionized water, affording the oil-in-water emulsion. The oil-in-water emulsion was added to a gelling bath in a manner analogous to example 12 wherein the gelling bath comprised of 7.2 grams of low molecular weight alginate (PROTANAL LFR 5/40 RB), 24.0 grams of low molecular weight PGA (Duckloid SLF-3, Kibun) 60.0 grams of glycerol (plasticizer), and 508.8 grams of deionized water. The gelling bath was maintained at ambient temperature during the addition and encapsulation of the oil-in-water emulsion. The emulsion was added to the gelling bath during 2 minutes, and after another 19 minutes in the gelling bath, the capsules were collected and rinsed in water for 5 seconds and then transferred to a hardening bath comprising 1.54 grams of Ca-lactate (Merck), 50 grams of glycerol (plasticizer) and 448.46 grams of deionized water. Capsules were left in the hardening bath for about 5 minutes. The capsules were dried on a bench with circulated air from a fan for 48 hours. After drying, the so-formed alginate-PGA capsules were oval in shape, measuring about 8 mm in diameter by about 14 mm in length and had a water content of 7.4%. The capsules comply with the European Pharmacopoeia disintegration test 01/2002:0016 for soft capsules using 0.1 M HCl as liquid medium.

EXAMPLE 16

Preparation and Alginate-Carrageenan-Propylene Glycol Alginate (PGA) Encapsulation of an Oil-in-Water Emulsion—Soy Oil: Acid Disintegrating Capsules An oil-in-water emulsion was prepared in a manner analogous to that of Example 4, wherein the oil-in-water emulsion was comprised of 480 grams of soybean oil, 20.0 grams of calcium chloride dihydrate, 4.0 grams of polyoxyethylene (20) sorbitan monolaurate (Emulsifier-Tween 20) and 40.0 grams of deionized water, affording the oil-in-water emulsion. A gelling bath comprised of 15.0 grams of low molecular weight alginate (PROTANAL LFR 5/60), 15.0 grams of kappa carrageenan (A-CAT, FMC Corporation), 60.0 grams of low molecular weight PGA (Duckloid SLF-3, Kibun) 150.0 grams of glycerol (plasticizer), and 1260.0 grams of deionized water was made by dissolving the alginate, carrageenan and PGA in the deionized water at 80° C. under vigorously stirring for 20 minutes. To 500 grams of the above-mentioned gelling bath, the emulsion was added in a manner analogous to example 12 during 2 minutes, and kept in the bath for another 19 minutes before they were collected and rinsed briefly in water. The gelling bath was maintained at 35° C. during the addition and encapsulation of the oil-in-water emulsion. The capsules were dried on a bench with circulated air from a fan for 48 hours, and after drying, the so-formed alginate-carrageenan-PGA capsules were oval in shape, measuring about 8 mm in diameter by about 13 mm in length. The capsules comply with the European Pharmacopoeia disintegration test 01/2002:0016 for soft capsules using 0.1 M HCl as liquid medium.

EXAMPLE 17

Preparation and Alginate-Polyvinyl Alcohol (PVA) Encapsulation of an Oil-in-Water Emulsion—Soy Oil: Acid Disintegrating Capsules An oil-in-water emulsion was prepared in a manner analogous to that of Example 4, wherein the oil-in-water emulsion was comprised of 269.8 grams of soybean oil, 10.0 grams of calcium chloride dihydrate, 2.0 grams of polyoxyethylene

(20) sorbitan monolaurate (Emulsifier-Tween 20) and 20.0 grams of deionized water, affording the oil-in-water emulsion. 24.1 grams of the oil-in-water emulsion was added to a gelling bath in a manner analogous to Example 12 wherein the gelling bath was comprised of 6.0 grams of low molecular weight alginate (PROTANAL LFR 5/60), 18.0 grams of Polyvinyl alcohol (PVA) (MW 30.000-70.000 Daltons, Sigma), 60.0 grams of glycerol (AnalR)(plasticizer), 120 grams of a 75% maltitol solution (Maltisweet 3145, 75%, SPI Polyols, USA) and 396.0 grams of deionized water. The emulsion was added to the gelling bath during 2 minutes, and kept in the bath for another 19 minutes before they were collected and rinsed briefly in water. The gelling bath was maintained at ambient temperature during the addition and encapsulation of the oil-in-water emulsion. The capsules were dried on a bench with circulated air from a fan for 48 hours, and after drying, the so-formed alginate-PVA capsules were oval in shape, measuring about 8 mm in diameter by about 13 mm in length. The capsules comply with the European Pharmacopoeia disintegration test 01/2002:0016 for soft capsules using 0.1 M HCl as liquid medium.

EXAMPLE 18

Preparation and Alginate-Cellulose Acetate Phthalate Encapsulation of an Oil-in-Water Emulsion: Enhancing Enteric Properties An oil-in-water emulsion was prepared in a manner analogous to that of Example 4, wherein the oil-in-water emulsion was comprised of 600 grams of soybean oil, 25.0 grams of calcium chloride dihydrate, 4.0 gram of polyoxyethylene(20) sorbitan monolaurate (Emulsifier-Tween 20) and 50.0 grams of deionized water, affording the oil-in-water emulsion. The above-mentioned oil-in-water emulsion was then added to a gelling bath in a manner analogous to example 12, wherein the gelling bath was comprised of 9.0 grams of higher weight-average molecular weight alginate (PROTANAL LF 10/60), 6.0 grams of low weight-average molecular weight alginate (PROTANAL LFR 5/60), 60.0 grams of glycerol (plasticizer), 12.0 grams of cellulose acetate phthalate (Eastman Chemical Company, USA) and 513.0 grams of deionized water, where the gelling bath was adjusted with 1 M NaOH-solution to pH 11. The addition to the gelling bath lasted for 2 minutes, and the forming capsules were kept in the bath for another 19 minutes before they were collected and rinsed briefly in water. The gelling bath was maintained at ambient temperature during the capsule formation. The capsules were dried in a manner analogous to that of Example 1, and after drying, the so-formed alginate capsules were oblong in shape, measuring about 7.5 mm in diameter by about 13 mm in length. The so-formed capsules comply with the European Pharmacopoeia test 01/2002:0013 for gastro-resistant capsules, using 50 mM phosphate buffer pH 6.8.

EXAMPLE 19

Preparation and Alginate Encapsulation of an Oil-in-Water Emulsion: High Solid Content-Calcium Carbonate An oil-in-water emulsion was prepared in a manner analogous to that of Example 4, wherein the oil-in-water emulsion was comprised of 80 grams of soybean oil, 4.0 grams of calcium chloride dihydrate, 1.0 gram of polyoxyethylene(20) sorbitan monolaurate (Emulsifier-Tween 20) and 10.0 grams of deionized water, affording the oil-in-water emulsion. A mixture of 35 grams of calcium carbonate (Merck) and 20 grams of the above-mentioned oil-in-water emulsion was then added to a gelling bath in a manner analogous to example 12, wherein the gelling bath was comprised of 9.0 grams of higher weight-average molecular weight alginate (PROTANAL LF 10/60), 6.0 grams of low weight-average molecular weight alginate (PROTANAL LFR 5/60), 60.0 grams of glycerol (plasticizer), and 525.0 grams of deionized water. The addition to the gelling bath lasted for 2 minutes, and the forming capsules were kept in the bath for another 19 minutes before they were collected and rinsed briefly in water. The gelling bath was maintained at ambient temperature during the capsule formation. The capsules were dried in a manner analogous to that of Example 1, and after drying, the so-formed alginate capsules were oblong in shape, measuring about 7.5 mm in diameter by about 12 mm in length and had a water content of 1.0%. The amount of calcium carbonate in the final dried capsules was calculated to 62%.

EXAMPLE 20

Preparation and Alginate Encapsulation of an Oil-in-Water Emulsion—Soy Oil: Stability of Dried Capsules An oil-in-water emulsion was prepared in a manner analogous to that of Example 4, wherein the oil-in-water emulsion was comprised of 1000 grams of soy oil, 50.0 grams of calcium chloride dihydrate, 10.0 grams of polyoxyethylene (20) sorbitan monolaurate (Emulsifier-Tween 20) and 100.0 grams of deionized water affording the oil-in-water emulsion. 132 grams of the prepared emulsion was then added in a manner analogous the Example 12 into a gelling bath comprised of 50.0 grams of higher weight-average molecular weight alginate (PROTANAL LF 10/60), 200.0 grams of low weight-average molecular weight alginate (PROTANAL LFR 5/60), 1000 grams of Sorbitol Special (SPI Polyols, USA) and 8750 grams of deionized water. The gelling bath was stirred at a moderate rate, while being maintained at a temperature of about 60° C. The addition of the emulsion was complete in about 2 minutes. Upon completion of addition, the so-formed alginate capsules were kept in the gelling bath for another 19 minutes. The capsules were strained form the bath and rinsed with water to remove non-reacted gelling bath. The capsules were dried in a manner analogous to Example 1. After drying the capsules were put into both closed and open plastic containers and inserted into an incubator at 40° C. and 75% relative humidity. During a period of 6 months the capsules were evaluated, and results are given in table 4 below. The capsules were of oval-type shape. Disintegration test was performed according to Ph. Eur. 4, 01/2002:0016, test for gastro resistant capsules, using 50 mM phosphate buffer pH 6.8.

TABLE 4

| Weeks | 0 | 4 | 4 | 12 | 12 | 26 | 26 |
|---|---|---|---|---|---|---|---|
| Container | Start | Open | Closed | Open | Closed | Open | Closed |
| Testing parameters | | | | | | | |
| Strength, Force 0.5 mm compression (g) | 1224 | 382 | 661 | 362 | 429 | 576 | 565 |
| STDEV (g), n = 5 | 66 | 221 | 198 | 45 | 48 | 102 | 33 |
| Strength, Force break (kg) | 16.7 | 12.2 | 16.4 | 13.4 | 12.9 | 13.7 | 15.2 |
| STDEV (kg), n = 5 | 3.7 | 3.8 | 1.8 | 2.9 | 3.8 | 2.4 | 3.1 |
| Dry Gel film thickness (in μm) | 150 | 110 | 110 | 110 | 110 | 130-140 | 130-140 |
| Oil leakage | None | None | None | None | None | None | None |
| Capsule breakage | None | None | None | 2/14 | None | 2/14 | None |
| Disintegration | Complies with test | Not tested | Not tested | Complies with test | Complies with test | Complies with test | Complies with test |

STDEV = standard deviation of measurements of 5 capsules.

EXAMPLE 21

Preparation and Alginate-Carrageenan Encapsulation of an Oil-in-Water Emulsion—Soy Oil: Stability of Dried Capsules An oil-in-water emulsion was prepared in a manner analogous to that of Example 4, wherein the oil-in-water emulsion was comprised of 109.5 grams of soy oil (Mills, Norway), 4.0 grams of calcium chloride dihydrate (Merck), 1.0 g Potassium chloride (Merck), 1.0 gram of polyoxyethylene(20) sorbitan monolaurate (Emulsifier-Tween 20) and 12.0 grams of deionized water, affording the emulsion. A part of the prepared emulsion was then added in a manner analogous to the one in Example 12 into a gelling bath comprised of 12.0 grams of low weight-average molecular weight alginate (PROTANAL LFR 5/60), 12.0 grams of kappa carrageenan (A-CAT, FMC Corporation) 60.0 grams of Sorbitol Special (SPI Polyols, USA) and 516 grams of deionized water. The gelling bath was stirred at a moderate rate, while being maintained at a temperature of about 60° C. The addition of the emulsion was complete in about 2 minutes. Upon completion of addition, the so-formed alginate-carrageenan capsules were kept in the gelling bath for another 19 minutes. The capsules were strained from the bath and quickly rinsed with water to remove non-reacted gelling bath. The capsules were dried in a manner analogous to Example 1. After drying the capsules were put into closed plastic containers and inserted into an incubator at 40° C. and 75% relative humidity. During a period of 6 months the capsules were evaluated, and results are given in table 5 below. The capsules were of oval-type shape. Disintegration test was performed according to Ph. Eur. 4, 01/2002:0016, test for soft capsules using 0.1 M HCl as liquid medium.

TABLE 5

| | Weeks | | | |
|---|---|---|---|---|
| Testing parameters | 0 | 4 | 12 | 26 |
| Strength, Force 0.5 mm compression (g) | 331 | 124 | 99 | 85 |
| STDEV (g), n = 5 | 16 | 10 | 19 | 5 |
| Strength, Force break (kg) | 9.1 | 8.6 | 8.6 | 4 |
| STDEV (kg), n = 5 | 2.2 | 1.1 | 0.9 | 1.3 |
| Dry Gel film thickness (in μm) | 170 | 210 | 230 | 220 |
| Oil leakage | None | None | None | None |
| Capsule breakage | None | None | None | None |
| Disintegration | Complies with test | Not tested | Complies With test | Complies with test |

STDEV = standard deviation of measurements of 5 capsules.

EXAMPLE 22

Preparation of an Oil-in-Water Emulsion—Soy Oil: Stability of Emulsion as Function of Time and Temperature An oil-in-water emulsion was prepared in a manner analogous to that of Example 4, wherein the oil-in-water emulsion was comprised of 520 grams of soy oil, 14.0 grams of calcium chloride dihydrate, 4.0 grams of polyoxyethylene(20) sorbitan monolaurate (Emulsifier-Tween 20) and 40.0 grams of deionized water, affording an oil-in-water emulsion. 5 measuring cylinders (25 ml) were filled to the top with about 30 grams of the emulsion, covered with parafilm and kept for 24 hours at 5° C., 20° C., 40° C., 60° C. and 80° C. and visually examined. No signs of destabilization were observed during this period for all temperatures. The emulsion in the cylinder kept at 80° C. was after 24 hours transferred to 20° C. and visually examined for another 35 days. No signs of destabilization were observed during this period.

EXAMPLE 23

Film Thickness, Variability, and Film Weight Versus Capsule Weight—Comparison with Commercially Available Gelatin Capsules An oil-in-water emulsion was prepared in a manner analogous to that of Example 4, wherein the oil-in-water emulsion was comprised of 131.5 grams of soy oil (Mills, Norway), 6.0 g of calcium chloride dihydrate (Merck), 1.0 grams of polyoxyethylene(20) sorbitan monolaurate (Emulsifier-Tween 20, Fluka) and 10.0 grams of deionized water, affording an oil-in-water emulsion. 19.8 grams of the prepared emulsion was then added in a manner analogous the Example 12, using a diameter of the hole of 6 mm, into a gelling bath comprised of 12.0 grams of higher weight-average molecular weight alginate (PROTANAL LF 10/60), 18.0 grams of low weight-average molecular weight alginate (PROTANAL LFR 5/60), 180.0 grams of glycerol (AnalR) and 990 grams of deionized water. The gelling bath was stirred at a moderate rate, while being maintained at a temperature of about 25° C. The addition of the emulsion was complete in about 2 minutes. Upon completion of addition, the so-formed alginate capsules were kept in the gelling bath for another 19 minutes. The capsules were strained from the bath and rinsed with water to remove non-reacted gelling bath. The capsules were dried in a manner analogous to Example 1, yielding oblong shaped capsules with a diameter of 6.8 mm and a length of 9.8 mm. The dried capsules had a total weight of about 250 milligrams, and a wall weight of about 41 milligrams. The total amount of water in the dried capsule was calculated to 6.2% by weight. Film thickness of the above described capsules and the capsules of Example 12 and Example 17 was compared with 4 commercially available gelatin capsules. The film thickness was obtained by measuring the film thickness of the cross-sectional cut of the capsules. Capsules were photographed using a Kappa CF 11/1 camera (Kappa messtechnik gmbh, Gleichen, Germany) on top of a Nikon SMZ-10 stereoscopic microscope (Nikon Corporation), printouts of the photographs were manually evaluated and film thickness was calculated at 8 equally spaced positions. The exception was capsules from Example 17, were the thin film made this methods difficult to perform and the capsule were measured directly at 8 equally spaced positions in a Nikon OPTIHOT microscope. The results are given in table 6 below. The average (AVE) and the relative standard deviation (% RSD) of the film thickness were calculated. The calculations of the film weight vs. the total weight (wt % Film) were for all capsules performed by dividing the film weight with the total capsule weight. The film weight was obtained after removing the contents of the capsules and thoroughly wiping the capsule shell clean.

TABLE 6

| Capsule | Manufacturer/batch | AVE (μm) | % RSD | wt % Film |
|---|---|---|---|---|
| Example 12 | FMC | 161 | 2.5 | 16 |
| Example 17 | FMC | 61 | 5.3 | 5.7 |
| Example 22 | FMC | 157 | 7.2 | 16 |
| Gelatine | Triomega ®, Pronova Biocare, 215741A | 452 | 16.2 | 32 |
| Gelatine, enteric | Mintec ™, Monmouth Pharmaceuticals Ltd, UK BN95822EC/1 | 526 | 13.9 | 39 |
| Gelatine | Möller's Dobbel, Peter Möller, Norway L93468 | 514 | 12.3 | 36 |
| Gelatine | Triomega Kids ®, Pronova Biocare, 4210104/1 TD3057 | 559 | 11.7 | 35 |

Those of ordinary skill in the art will appreciate that variations of the invention may be used and that it is intended that the invention may be practiced otherwise than as specifically described herein. Accordingly, the invention includes all modifications encompassed within the spirit and scope of the invention as defined by the following claims.

The invention claimed is:

1. A method of preparing seamless capsules having a polysaccharide gel membrane on the outer surface, comprising the steps of:
   (a) preparing an emulsion comprising oil, water, an emulsifier, and at least one of a water-soluble monovalent metal salt, polyvalent metal salt, and an acid, wherein said oil is present in an amount of at least 50% by weight of said emulsion and said emulsion is an oil-in-water emulsion; with the proviso that said emulsion does not contain marmelo mucilage; and
   (b) adding portions of said emulsion to an aqueous gelling bath comprised of at least one ionic polysaccharide thereby encapsulating said portions of said emulsion in a polysaccharide gel membrane,
   (c) optionally drying the resulting capsules by removing water and optionally applying a coating to the outer surface of said gel membrane;
   wherein said polysaccharide comprises an alginate, said capsule is enteric or delayed release, and said capsule is oblong, oval or cylindrical.

2. The method of preparing the seamless capsules of claim 1, further comprising the step of:
   adding a further solid, or liquid or gaseous component prior to step b) to at least one of said oil, water, emulsifier and at least one water-soluble monovalent metal salt, polyvalent metal salt, and acid prior to or after formation of the emulsion and mixing to a dispersion.

3. The method of claim 1, wherein said emulsion further contains a pharmaceutical active agent, a veterinary active agent, a nutritional supplement, an agricultural active agent, cosmetic ingredient, colorant or a food.

4. A method of claim 2, wherein said solid, or liquid or gaseous component is selected from the group consisting of a pharmaceutical active agent, a veterinary active agent, a nutritional supplement, an agricultural active agent, a cosmetic ingredient, colorant and a food.

5. A method of claim 3, wherein the amount of components added to the emulsion of said oil, water, emulsifier and at least one water-soluble monovalent metal salt, polyvalent metal salt, and acid, is present in amounts up to 85% by weight of the dried capsule.

6. A method of claim 5, wherein the amount of components added to the emulsion of said oil, water, emulsifier and at least one water-soluble monovalent metal salt, polyvalent metal salt, and acid, is present in amounts from 30% up to 85% by weight of the dried capsule.

7. The method of claim 1, wherein said oil is present in said oil-in-water emulsion in an amount of 70% by weight to 98% by weight of said oil, water, emulsifier and at least one water-soluble monovalent metal salt, polyvalent metal salt, and acid.

8. The method of claim 7, wherein said oil is present in said oil-in-water emulsion in an amount of 85% by weight to 95% by weight of said oil, water, emulsifier and at least one water-soluble monovalent metal salt, polyvalent metal salt, and acid.

9. The method of claim 1, wherein said water-soluble monovalent or polyvalent metal salt is present in an amount of up to 25% by weight of said oil, water, emulsifier and at least one water-soluble monovalent metal salt, polyvalent metal salt, and acid.

10. The method of claim 9, wherein said salt is present in an amount of 2% by weight to 15% by weight of said oil, water, emulsifier and at least one water-soluble monovalent metal salt, polyvalent metal salt, and acid.

11. The method of claim 1, wherein said emulsifier has a hydrophilic-lipophilic balance (HLB)- value in the range of 1 to 19.

12. The method of claim 11, wherein said emulsifier is polyoxyethylene(20) sorbitan monolaurate, polyglycerol polyricinoleate, calcium stearoyl-2-lactylate, sorbitan monooleate, or mixtures thereof.

13. The method of claim 12, wherein said emulsifier is polyoxyethylene(20) sorbitan monolaurate, polyglycerol polyricinoleate, or mixtures thereof.

14. The method of claim 1, wherein said water-soluble monovalent or polyvalent metal salt is at least one salt of sodium, potassium, calcium, strontium, barium, magnesium, and aluminum.

15. The method of claim 14, wherein said salt is calcium chloride.

16. The method of claim 1, wherein said at least one ionic polysaccharide is present in an amount of from 0.1% by weight to 10% by weight of the gelling bath.

17. The method of claim 16, wherein said weight of said at least one ionic polysaccharide is from 0.5% by weight to 7% by weight, preferably 1% by weight to 5% by weight of the gelling bath.

18. The method of claim 1, wherein the gelling bath further comprises one or more secondary film former in an amount up to 40% by weight of the gelling bath.

19. The method of claim 18, where the secondary film former is selected from the group of cellulose acetate phthalate, cellulose acetate succinate, methyl cellulose phthalate, ethylhydroxycellulose phthalate, polyvinylacetatephtalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, or mixtures thereof.

20. The method of claim 18, where said secondary film former is selected from the group of propylene glycol alginate, polyvinyl alcohol, carrageenans, pectins, chitosans, guar gum, gum acacia, sodium carboxymethylcellulose, hydroxypropylmethyl cellulose, hydroxypropylcellulose, methylcellulose, starches, maltodextrins, or mixtures thereof.

21. Method of claim 1, wherein said capsules are washed with an aqueous solution, or an aqueous solution of alcohol after encapsulation.

22. The method of claim 1, wherein said at least one ionic polysaccharide is an alginate having a weight-average molecular weight of 20,000 Daltons to 500,000 Daltons.

23. The method of claim 1, wherein said at least one ionic polysaccharide is a mixture of (i) an alginate having a weight-average molecular weight of 30,000 Daltons to 40,000 Daltons, and (ii) an alginate having a weight-average molecular weight of 150,000 Daltons to 500,000 Daltons.

24. The method of claim 23, wherein said mixture of (i) and (ii) is in a ratio of 0.1 to 20 of (i) to 1 of (ii), respectively.

25. The method of claim 24, wherein said ratio is 1 to 16 of (i) to 1 of (ii), respectively.

26. The method of claim 22, wherein said alginate has a G content of at least 30%.

27. The method of claim 26, wherein said G content is 40% to 80%.

28. The method of claim 1, wherein said gelling bath is maintained at a temperature of at least 20° C. during step (b).

29. The method of claim 28, wherein said temperature is in the range of 30° C. to 70° C.

30. The method of claim 1, wherein said addition in step (b) is conducted during a period of time of up to 240 minutes.

31. The method of claim 30, wherein said period of time is from 2 minutes to 60 minutes.

32. The method of claim 31, wherein said period of time is from 5 minutes to 20 minutes.

33. The method of claim 1, further comprising coating said capsules with a secondary film-former, or a sequestrant, or a secondary film-former and a sequestrant.

34. The method of claim 33, wherein said coating is conducted simultaneously with a step of drying said capsules.

35. Seamless capsule having a polysaccharide gel membrane on the outer surface, prepared by a method comprising the steps of:
  (a) preparing an emulsion comprising oil, water, an emulsifier, and at least one of a water-soluble monovalent metal salt, polyvalent metal salt, and an acid, wherein said oil is present in an amount of at least 50% by weight of said emulsion and said emulsion is an oil-in-water emulsion; with the proviso that said emulsion does not contain marmelo mucilage;
  (b) adding portions of said emulsion to an aqueous gelling bath comprised of at least one ionic polysaccharide thereby encapsulating said portions of said emulsion in a polysaccharide gel membrane, and
  (c) optionally drying the resulting capsule by removing water and optionally applying a coating to the outer surface of said gel membrane;
  wherein said polysaccharide comprises an alginate, said capsule is enteric or delayed release, and said capsule is oblong, oval or cylindrical.

36. Seamless capsule of claim 35, further comprising the step of:
  adding a further solid, or liquid or gaseous component prior to step b) to at least one of said oil, water, emulsifier or at least one water-soluble monovalent metal salt, polyvalent metal salt, and acid prior to or after formation of the emulsion and mixing to a dispersion.

37. Seamless capsule of claim 36, wherein said solid, or liquid or gaseous component is selected from the group consisting of a pharmaceutical active agent, a veterinary active agent, a nutritional supplement, an agricultural active agent, a cosmetic ingredient, colorant and a food.

38. Seamless capsule of claim 37, wherein the amount of components added to the emulsion is present in amounts up to 85% by weight of the dried capsule.

39. Seamless capsule of claim 38, wherein the amount of components added to the emulsion is present in amounts from 30% up to 85% by weight of the dried capsule.

40. Capsule of claim 35, wherein said gel membrane further comprises one or more secondary film formers selected from cellulose acetate phthalate, cellulose acetate succinate, methyl cellulose phthalate, ethylhydroxycellulose phthalate, polyvinylacetatephtalate, polyvinylbutyrate acetate, vinyl acetate-maleic anhydride copolymer, styrene-maleic monoester copolymer, methyl acrylate-methacrylic acid copolymer, methacrylate-methacrylic acid-octyl acrylate copolymer, or mixtures thereof.

41. Capsule of claim 35, wherein said gel membrane further comprises one or more secondary film formers selected from propylene glycol alginate, polyvinyl alcohol, carrageenans, pectins, chitosans, guar gum, gum acacia, sodium carboxymethylcellulose, hydroxypropylmethyl cellulose, hydroxypropylcellulose, methylcellulose, starches, maltodextrins or mixtures thereof.

42. The seamless capsule of claim 35, wherein said oil is a pharmaceutical agent or a nutritional supplement.

43. The seamless capsule of claim 35, wherein said oil comprises at least one of fatty acids, esters or derivatives thereof.

44. The seamless capsule of claims 35, wherein said oil is fish oil.

45. The seamless capsule of claim 35, wherein said oil is derived from animals, plants or microorganisms.

\* \* \* \* \*